(12) United States Patent
Lee et al.

(10) Patent No.: US 6,740,036 B1
(45) Date of Patent: May 25, 2004

(54) OPTICAL AND ULTRASOUND PROBE FOR MONITORING BLOOD VOLUME CHANGES

(76) Inventors: Lian-Pin Lee, 2017 Echo Ridge Rd., Charlottesville, VA (US) 22911; Jen-Shih Lee, 2017 Echo Ridge Rd., Charlottesville, VA (US) 22911

( * ) Notice: Subject to any disclaimer, the term of this patent is extended or adjusted under 35 U.S.C. 154(b) by 80 days.

(21) Appl. No.: 10/274,086

(22) Filed: Oct. 18, 2002

Related U.S. Application Data

(63) Continuation-in-part of application No. 09/908,223, filed on Jul. 18, 2001, now Pat. No. 6,485,427
(60) Provisional application No. 60/218,906, filed on Jul. 18, 2000.

(51) Int. Cl.[7] .................................................. A61B 8/00
(52) U.S. Cl. ....................................... 600/437; 210/739
(58) Field of Search ............................... 600/437, 443, 600/447, 448, 449; 210/739, 646; 73/861.02; 128/916

(56) References Cited

U.S. PATENT DOCUMENTS

| | | | |
|---|---|---|---|
| 5,230,341 A | | 7/1993 | Polaschegg |
| 5,312,550 A | | 5/1994 | Hester |
| 5,453,576 A | | 9/1995 | Krivitski |
| 5,499,627 A | | 3/1996 | Steuer et al. |
| 5,685,989 A | | 11/1997 | Krivitski et al. |
| 5,830,365 A | | 11/1998 | Schneditz |
| 6,117,099 A | | 9/2000 | Steuer et al. |
| 6,149,595 A | * | 11/2000 | Seitz et al. ................ 600/438 |
| 6,461,586 B1 | * | 10/2002 | Unger ....................... 424/9.32 |
| 6,503,203 B1 | * | 1/2003 | Rafter et al. ............... 600/458 |

* cited by examiner

*Primary Examiner*—Marvin M. Lateef
*Assistant Examiner*—Maulin Patel
(74) *Attorney, Agent, or Firm*—Parker & DeStefano

(57) ABSTRACT

An apparatus and method to assess the compressibility, density, and hematocrit of blood including an optical ultrasound probe clipped onto tubing in which blood is flowing. The probe includes a combination of ultrasound transducers, a light emitting diode, and photodiodes. An indicator medium is injected into the bloodstream of the subject over one or more time points. Ultrasound waves are emitted by a transducer and received by another transducer, and a novel signal-processing unit and a computer with a novel computation scheme process the ultrasound signals to assess the phase shift of ultrasound as it transmitted across the blood stream. Based on the linear relationship between compressibility and density, changes in blood density are calculated from changes in phase shift. The optical part of the probe assesses the hematocrit of blood. Two fluid media are used to calibrate the probe on the relationship between phase shift and density in the factory. Before clinical assessment, an on-line saline injection procedure and the resulting change in density is employed to calibrate the optical density of the optical probe in terms of hematocrit and to establish the interrelation between density and hematocrit on fluid dilution of the circulating blood. One clinical protocol to monitor blood volume and microvascular pooling employs saline infusion to determine the blood volume hourly and the density and hematocrit measurements to determine the change in blood volume and the volume pooled to the microcirculation. Another clinical protocol assesses the time course of hematocrit and density over hemodialysis treatment for the prediction of hypovolemia and microvascular pooling. This cardiovascular monitoring is useful for evaluating how complications are developed during hemodialysis or the adequacy of any post-trauma fluid replacement or therapy to alleviate the complications.

21 Claims, 6 Drawing Sheets

OPTICAL AND ULTRASOUND PROBE FOR MONITORING BLOOD VOLUME CHANGES

RELATED U.S. APPLICATIONS

This application is a continuation-in-part of U.S. patent application Ser. No. 09/908,223 filed Jul. 18, 2001 now U.S. Pat No. 6,485,427 which claims the priority of U.S. Provisional Application 60/218,906, filed Jul. 18, 2000.

FIELD OF THE INVENTION

This invention relates to systems and methods for microinvasive, continuous monitoring of a patient's changes in blood density and hematocrit in order to determine the blood volume and microvascular pooling of the patient over time to better profile the patient's response to hemodialysis, trauma, or burn injury and to achieve more effective diagnosis and treatment.

BACKGROUND

An apparatus and method are described to monitor the time of sound transmission in the blood stream of a patient, to use a linear relationship between compressibility and density for accurate and sensitive assessment of blood density changes, and to employ optical density for assessment of hematocrit changes due to dilution by saline, dialysate or therapeutic changes. Through appropriate clinical protocols, the density and hematocrit changes are used individually or in combined form to determine the plasma protein concentration, blood volume, change in blood volume, and microvascular pooling of the patient over time.

Hypotension and hypovolemia are common circulatory problems that occur during shock (Chien et al, *American Journal of Physiology*, 210:1411–1418), traumatic injury, dialysis (Amerling et al in *Clinical Dialysis* $3^{rd}$ Edition, Appleton and Lang editors, 1995) and surgical interventions. A variety of disorders and injuries are related to the occurrence of hypotension (Daugirdas, *Kidney International* 39:233–246). Fluid loss related to burn injury or hemorrhage due to trauma is examples of situations where compensation for such loss is necessary. Infusing isotonic saline, plasma or other physiological solutions into the circulation until arterial pressure is elevated to normal is usually employed as the treatment. Although blood volume reduction correlates with reduction in arterial pressure under laboratory simulations of injury and anesthesia, actual occurrences of traumatic blood loss often show only slightly reduced arterial pressures due to the body's neural compensation mechanisms. Once these mechanisms reach their limits, arterial pressure can drop rapidly. The management of this subnormal arterial pressure is critical to survival; immediate restoration of arterial pressure after traumatic injury can cause more problems than allowing the pressure to remain subnormal. Rapid restoration of arterial pressure results in higher oxygen demand and the increase in blood flow may dislodge clots to cause stroke.

While the body's compensation mechanisms are important to survival, limitations exist in the ability to determine several factors including the volume of blood loss, the distribution of blood volume between the microcirculation and macrocirculation, the necessary volume for infusion, and whether overexpansion of the blood volume has occurred after infusion. Arterial pressure monitoring is unable to provide sufficient information to address these concerns. A need exists for precise monitoring of changes to blood volume and microvascular pooling in patients, particularly over extended time periods.

Beyond trauma and burn injury, a number of medical conditions require such precise monitoring of blood volume. Invasive surgery and dialysis are two common situations where monitoring blood volume changes provide important information related to the outcome of the surgery and dialysis. For example, about 30% of patients undergoing dialysis in the United States will experience hypotension and, occasionally, circulatory shock. Milder symptoms include muscle cramping and lightheadedness. These dialysis related side effects are implicated in reduced dialysis efficacy.

Dialysis and systems for dialysis are well known in the art. These work by extracting a significant fraction of fluid from the circulating blood. Compensation for this reduction in blood volume normally occurs through fluid restituted from the tissue. The activation of the microcirculation by hemodialysis leads to pooling of blood in the microcirculation affecting a low venous return, poor cardiac filling, lowered cardiac output and then hypotension. For patients undergoing a well-controlled fluid removal, these cardiovascular changes and hypovolemia are the reason for hypotension development during the course of hemodialysis. Using saline or dialysate dilution, we can monitor the change in blood volume over times, for example every half hour. A continuous change in blood density can be analyzed and microvascular pooling within the circulation can be determined. These parameters can be used by physicians to carefully monitor the cardiovascular changes that are responsible for the development of hypotension in dialysis patients.

When patients undergo hemodialysis or are subject to trauma or burns, there is significant exchange of fluid and protein between the tissue and blood compartment. These exchanges will alter the plasma protein concentration. Consequently an on-line system capable of monitoring changes in plasma protein concentration will be valuable to the physician in selecting an appropriate fluid therapy to compensate for the loss of plasma and/or plasma protein. Currently no system can assess on-line and clinically monitor plasma protein concentration.

The use of sound velocity measurements in blood to assess blood volume has been attempted and described previously. Krivitski, in U.S. Pat. Nos. 5,453,576 and 5,685,989 describes an apparatus and method for measuring several hemodynamic parameters by using a sound velocity sensor. The information contained in the '576 and the '989 patent is incorporated by reference as though cited in its entirety. The technique described uses a linear approximation of a non-linear relationship between the sound velocity and the density of the blood. This approximation introduces additional error into the volume computation, which limits the accuracy of the system. Further, the '576 patent is limited to large variations in sound velocity which make it inaccurate to assess blood volume.

The system patented by Schneditz in U.S. Pat. No. 5,830,365 also utilizes sound velocity for the measurement of total protein concentration, and then the blood volume by altering the dialyzer to run at a different ultrafiltrate extraction rate. These two methods are limited to large variations in sound velocity and the requirement of no blood pooling to the microcirculation.

Several other devices exist which are used to monitor blood volume or blood parameter changes. These include the Know-Recirc™ hematocrit measurement device produced by H&H Control Systems (Jackson, Miss.) and described in U.S. Pat. No. 5,312,550 and an optical device marketed under the Crit-Line® platform and the Transcutaneous Access Flow device by HemaMetrics Corporation (Boston, Mass.) described in U.S. Pat. Nos. 5,499,627 and 6,117,099. These devices continuously monitor the change in hematocrit over a dialysis session. Increases in hematocrit over the session are interpreted as a decrease in plasma volume thereby theoretically providing a mechanism for monitoring blood volume changes. This method does not account for the Fahraeus effect where microvascular pooling of blood can result in an increase in hematocrit. By not correcting for microvascular pooling, blood volume changes estimated by this device are off by a factor of two or more. Again, sensitivity of this device is limited and can cause incorrect diagnoses or treatments. Daugirdas (*American J. Kidney Disease*, 38:S11–S17, 2001) commented that none of these hematocrit approaches are successful because the conclusion from the measured hematocrits exhibits considerable interpatient and intrapatient variability. A similar problem exists in the work of Polaschegg in U.S. Pat. No. 5,230,341. Correction for microvascular pooling and sensitivity are deficient in the '341 patent and incorrect results on the projected blood volume occur leading to potentially harmful treatments.

SUMMARY OF THE INVENTION

The present invention provides a method and an optical/ultrasound probe to accurately and reliably determine compressibility, density, hematocrit, and plasma protein concentration, and the changes of these blood parameters due to the infusion of saline or dialysate for the quantification of blood volume or microvascular pooling in patients. The invention utilizes the changes of blood density and hematocrit over time while accounting for the effect of the microcirculation to provide medical professionals with valuable information on microvascular pooling and hypovolemia for the prevention of complications related to trauma and hemodialysis.

Further, the present invention measures through the ultrasound probe and a signal processing unit the phase shift between emitting ultrasound and receiving ultrasound, converts the phase shift to transmssion time and subsequently to sound velocity of blood flowing in a corporeal or extracorporeal system, and uses the linear relationship between compressibility and density to calculate from sound velocity the compressibility and density of blood.

The novel embodiments of the optical ultrasound probe provide significant advantages over the prior art. These include:

(1) A simpler hardware and software to detect phase shift of ultrasound signals for the determination of sound velocity;

(2) A factory procedure to calibrate the relationship between the sound velocity and density of blood on using the ultrasound probe to determine density;

(3) A set of computer files and equations to account for the dependence of density and sound velocity of blood on temperature;

(4) An on-line method using the ultrasound probe to calibrate the optical density of the optical probe for the determination of hematocrit;

(5) The combined use of the hematocrit and density measurement for the determination of plasma protein concentration;

(6) A data averaging procedure to better define the time course of density, hematocrit, and plasma protein concentration and to better characterize the interrelation between hematocrit and density changes;

(7) A graphic organization of the hematocrit and density measurements to differentiate whether a therapeutic process induces the patient to produce hypovolemia, microvascular pooling or both;

(8) An on-line analysis and procedure to quantify the time course of microvascular pooling, blood volume, and plasma protein concentration.

The combination of these eight features enables the optical/ultrasound probe to be produced at low cost, to achieve accurate assessments and to provide crucial information for the physician to select an effective strategy to prevent or treat hypotension in any patient.

Blood is a mixture of cells and plasma. The density and compressibility of blood is the sum of its components weighted by the volume fraction. The velocity of ultrasound in blood is related to a variety of factors, including the hematocrit, blood and plasma density, plasma protein concentration, and total protein concentration of blood. Likewise, blood compressibility also relates to these physical parameters of blood and plasma. These relationships are difficult to identify because of a lack of accurate measurement systems. Attempts at relating variable factors have deduced approximations to be utilized by the system described in the '576 patent and in the Know-Recirc™ and the Crit-Line® hematocrit measurement system. These empirical approximations limit the accuracy of the measurement systems and introduce errors into the data analysis.

The more accurate calculation of blood volume and the determination of its distributions within the circulation taught herein are used to monitor and treat patients more effectively. Software and hardware are configured to generate and receive the ultrasound wave and light and use the information to monitor the changes in plasma protein concentration and redistribution of blood volume in patients. Methods for interfacing the data generated by the monitoring technique on the transmission of sound, absorption and reflection of light with analytical machinery will become apparent to those of skill in the art based on the description contained herein.

DESCRIPTION OF THE PREFERRED EMBODIMENTS

Figure 1:
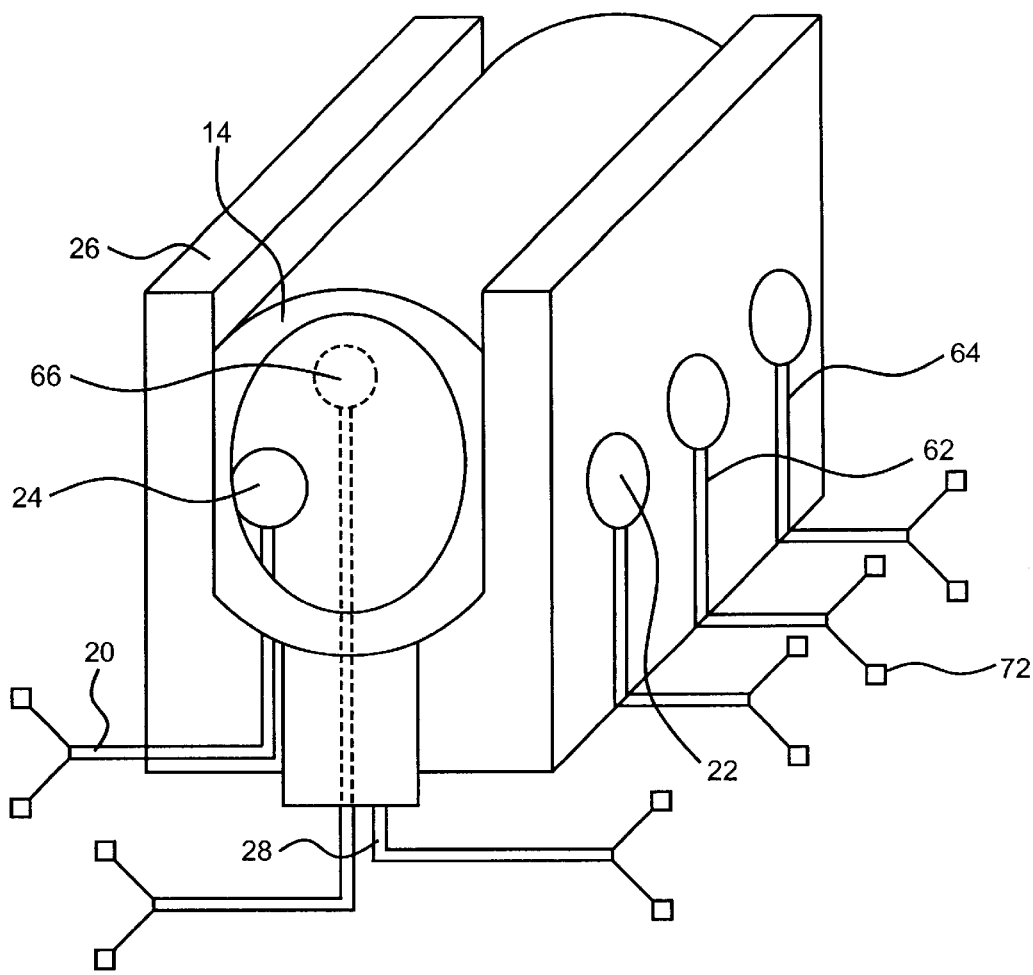
FIG. 1 is a schematic drawing of an embodiment of the optical ultrasound probe. It has a pair of ultrasound transducers, a light emitting diode and two photodiodes, and a thermistor. The probe is clipped on to a tube with flowing blood. In this design, the transducers, diodes and thermistor have no direct contact with the blood.

FIG. 1 shows an embodiment of the ultrasound optical probe. In this embodiment, the probe exists in a clip 26, which is mounted with the ultrasound emitting transducer 22, the receiving transducer 24, the light-emitting diode 62, the photodiode 64 for reflectance measurement, and the photodiode 66 for absorbance measurement. The surfaces of the transducers 22 and 24 and diodes 62, 64 and 66 are directly in contact with a tubing 14 inserted into the clip 26. The tubing 14 is connected to an extracorporeal circuit from which the flowing fluid (blood, plasma or saline) is used for the measurement.

Figure 3:
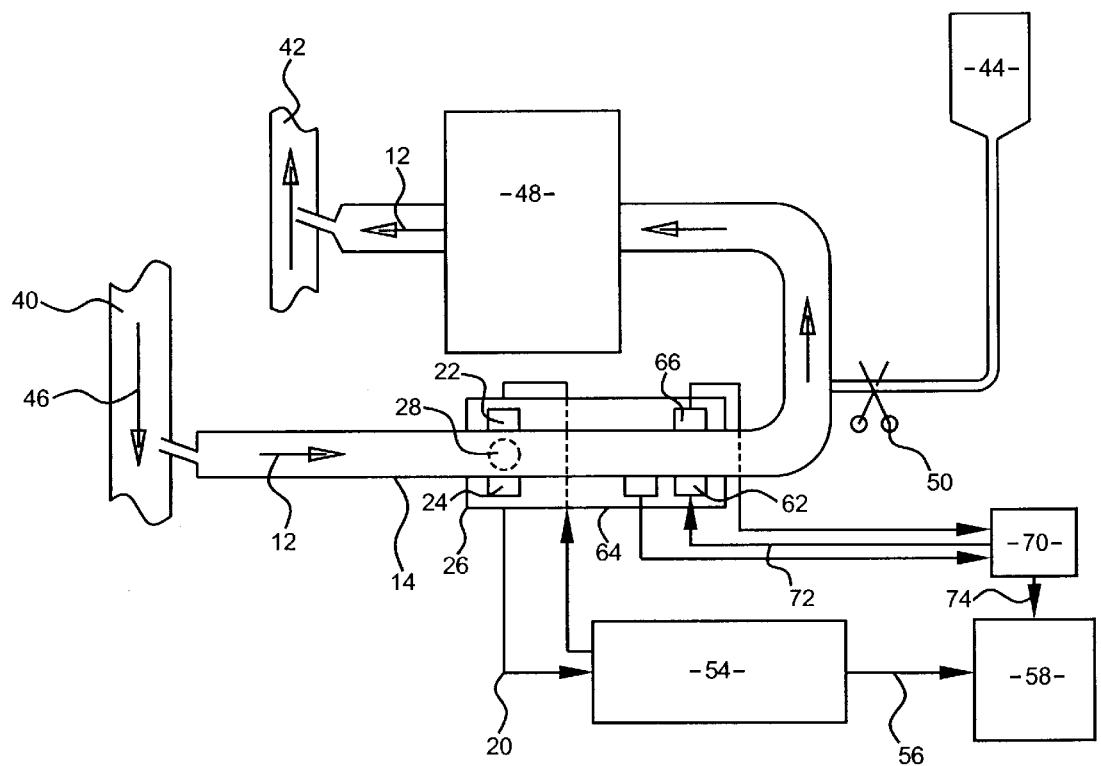
FIG. 3 is a schematic drawing of the optical ultrasound probe as it is used to measure compressibility, density and hematocrit of blood flowing through the tubing of an extracorporeal system connected to the patient.

Cabling and connectors 20 transmit power from a signal generator within the ultrasound signal-processing unit 54 to activate the emitting transducer 22 into producing a continuous wave of ultrasound at a frequency of about 3 to 5 Megahertz. The power signal is digitized as the excitation signal by one channel of a dual channel analog-to-digital (A/D) converter within the ultrasound signal-processing unit 54, which is shown in FIG. 3. The receiving transducer 24 receives the ultrasound wave produced by emitting transducer 22 and sends it to the other channel of the dual channel A/D converter for digitization. Both the digitized excitation and receiving signals are sent via cable 74 to the computer 58 shown in FIG. 3 for the determination of the phase shift of the receiving signal from the excitation signal.

In this embodiment, the clip 26 has a gap about 5 mm for the insertion of the tubing 14 whose outside diameter is about 6.2 mm. Tubing with a diameter other than 6.2 mm can be used in the system and the dimensioning adjustments to the clip will be obvious to those skilled in the art. The adjustment will be incorporated through the parameters stored in a data file accompanying the probe. Ultrasound gel is used to facilitate the insertion of the tubing 14 into the clip and to provide an airtight contact between the tubing 14 and the transducers 22, 24, preventing errors that can be caused by the reflection of ultrasound through air bubbles likely trapped between the transducers and tubing.

A power source within an optical signal-processing unit 70 sends a driving power through cable 72 to activate the photodiode 62 to emit light with a wavelength of 805 nm. The signals from the photodiodes 64 and 66 are then digitized by a dual channel A/D converter within the optical signal-processing unit 70 and are sent to computer 58 for the determination of the optical density and subsequently, through the equations discussed herein, the change in hematocrit of the blood flowing in the tubing 14. A thermistor 28 measures the temperature of flowing blood. The entire optical ultrasound probe 26 is housed in an insulator to assure the temperature at the thermistor 28 is identical to that of the flowing blood.

The information obtained by the ultrasound transducers is sent through the ultrasound signal-processing unit to a computer, which incorporates a new computation scheme and a novel linear relationship between compressibility and density to carry out the computation from the measurement of phase shift of blood. The following linear relationship, deduced from the fact that blood is a mixture of protein and ultrafiltrate, describes the dependence of the compressibility ($\hat{e}$) on the density ($\tilde{n}$) by a slope (b) and an x-intercept (a) as in Equation 1.

$$\kappa = a + b\rho \qquad \text{Equation 1}$$

This relationship holds over a wide range of hematocrit, plasma protein concentration, and total protein concentration of blood, blood density, and plasma density. The propagation velocity of ultrasound c and the density in blood are related to compressibility as shown in Equation 2.

$$\kappa = \rho/c^2 \qquad \text{Equation 2}$$

We can combine Equation 1 and 2 to obtain a quadratic equation for solving the density and compressibility from the measured sound velocity. Tests with the ultrasound transducer system described herein and a system that measures directly the density demonstrate that the density and sound velocity are related by the quadratic equation so derived.

The ultrasound signal-processing unit sends out a signal to excite a transducer to emit ultrasound at a frequency (f) of 3 to 5 Megahertz. After the transmission of the ultrasound through the tube wall and blood medium, a receiving transducer picks up the ultrasound. The hardware employed in the ultrasound signal-processing unit has a dual channel A/D converter to convert the excitation signal and receiving signal to digitalized forms at a sampling frequency of 65 or 105 mega samples per second (MSPS). These samples, identified respectively as $E_i$ and $R_i$ with i being the sampling index, are stored on the computer. After a period of time, the sampled data are multiplied and summed according to the computation scheme defined by Equations 3 and 4:

$$M_1 = \hat{O}(E_i R_i) \text{ with the summation from } i=1 \text{ to } N \qquad \text{Equation 3}$$

$$M_2 = \hat{O}(E_{i+j} R_i) \text{ with the same summation as above} \qquad \text{Equation 4}$$

where j is chosen to shift the phase of the emitting signal by 90 degrees in accordance with the frequency of excitation and sampling frequency. The total number N used for the summation is chosen to be an integer multiple of 4j to cover N/(4j) cycles of the ultrasound. Then we determine the phase shift of the receiving signal from the emitting signal as:

$$\ddot{o} = \tan^{-1}(M_2/M_1) \qquad \text{Equation 5}$$

where $\ddot{o}$ is expressed in the unit of degree.

Figure 2:
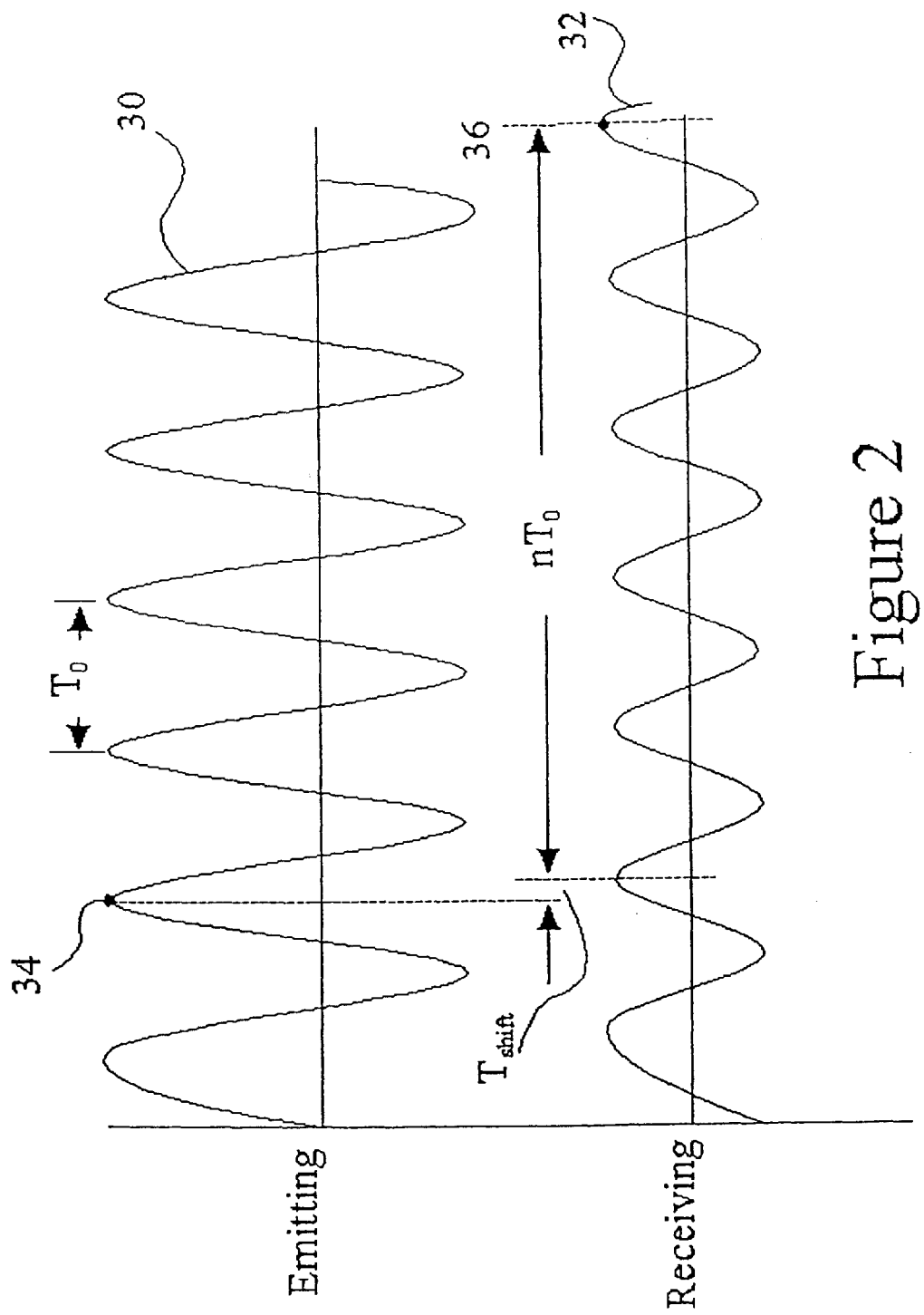
FIG. 2 is an illustration identifying the phase and time shift of the receiving ultrasound from the emitting ultrasound. The signal processing unit will first assess the relative phase shift of the sound waves and then through a factory calibration procedure to obtain the overall phase shift, which is used to compute the sound velocity, compressibility and finally density of blood.

FIG. 2 shows the time and phase shift between the emitting ultrasound and receiving ultrasound. With the use of continuous wave, the time of each oscillation ($T_0$) is 1/f and the relative time shift of the receiving signal from the emitting one ($T_{shift}$) is $\ddot{o}/(f \cdot 360°)$. However, the peak-to-peak time shift of the receiving signal from the excitation signal has an offset (an integer number n of ultrasound oscillations) from the phase shift of Equation 5. This offset is equivalent to adding $n \cdot 360°$ to the phase shift $\ddot{o}$.

Let the phase shift and sound velocity of saline, hypertonic saline, and blood be identified as $\ddot{o}_s$, $c_s$, $\ddot{o}_h$, $c_h$, $\ddot{o}_b$ and $c_b$ respectively. The time for the ultrasound to transmit from the emitting transducer to the receiving one relates for each medium to its phase shift by these equations:

$$\ddot{o}_s + n \cdot 360° = f \cdot 360° \cdot (L/c_s + 2h/c_w) \qquad \text{Equation 6}$$

$$\ddot{o}_h + n \cdot 360° = f \cdot 360° \cdot (L/c_h + 2h/c_w) \qquad \text{Equation 7}$$

$$\ddot{o}_b + n \cdot 360° = f \cdot 360° \cdot (L/c_b + 2h/c_w) \qquad \text{Equation 8}$$

where h is the wall thickness of the tube inserted into the trough of the HDM probe, L+2h is the distance between the transducers, and $c_w$ is the sound velocity of the tube wall. Subtracting these equations to eliminate $c_w$ and solving for the sound velocity of blood, we have $$c_s/c_b = 1 - (1 - c_s/c_h)(\ddot{o}_b - \ddot{o}_s)/(\ddot{o}_h - \ddot{o}_s) \quad \text{Equation 9}$$

The use of this velocity ratio in the following quadratic equation solves the blood density:

$$1 - (c_s/c_b)^2 = (b-1)(\tilde{n}_b/\tilde{n}_s - 1) + b(\tilde{n}_b/\tilde{n}_s - 1)^2 \quad \text{Equation 10}$$

To obtain a more explicit equation relating the density and phase shift, we will reference our measurement to that of a whole blood, which has a density of 1045 g/l at 37° C. Generated from Equation 9 and the linearized version of Equation 10 around the reference blood density ($\rho_{ref}$), we can determine the blood density ($\rho_b$) by Equation 11.

$$\rho_b = \tilde{n}_{ref} + \rho_s G(\phi_b - \ddot{o}_{ref})/(\ddot{o}_h - \ddot{o}_s) \quad \text{Equation 11}$$

where $\ddot{o}_{ref}$ is the phase shift of the reference blood and the constant G is given by Equation 12.

$$G = 2(c_s/c_{ref})(1 - c_s/c_h)/[(b-1) + 2b(\rho_{ref} - \tilde{n}_s)/\tilde{n}_s] \quad \text{Equation 12}$$

To determine the integer n in Equations 6 to 8, we will measure the change in phase $\ddot{A}\ddot{o}_s$ following a small increment in the ultrasound frequency by $\ddot{A}f$. The application of Equation 6 to this scenario yields Equation 13 to relate the phase and frequency change.

$$\ddot{A}\ddot{o}_s = \ddot{A}f \cdot 360° \cdot (L/c_s + 2h/c_w) \quad \text{Equation 13}$$

After the division of Equation 13 by Equation 6, we reorganize the result to Equation 14 for the determination of n.

$$n = \text{Round}[(f\ddot{A}\ddot{o}_s/\ddot{A}f - \ddot{o}_s)/360°] \quad \text{Equation 14}$$

where the function "Round" stands for the rounding of number in [0] to its nearest integer.

The parameters in Equations 9 to 12 are dependent on the temperature. The dependence of G on the temperature can be approximated by Equation 15.

$$G = G_0[1 - G_1(T - 37° C.)] \quad \text{Equation 15}$$

For the isotonic and hypertonic saline employed in the calibration and the blood chosen as the reference, the constant $G_0$ is about 0.06 and the constant $G_1$ is about 0.0033. The factory will pre-calibrate a given probe and include in the data file the value of n and the temperature dependence of $\ddot{o}_s$, $\ddot{o}_{ref}$, $\ddot{o}_h - \ddot{o}_s$, $\tilde{n}_s$ and $\tilde{n}_{ref}$. The computation scheme and the ultrasound signal processing unit of the present invention can be incorporated with the compressibility probe described in U.S. patent application Ser. No. 09/908,223 filed Jul. 18, 2001, to which the present application claims priority, to improve the functionalities of the compressibility probe to determine fluid density.

In general the data file will contain data to cover a wide spectrum of tubing that is used in hemodialysis machines of various manufacturers. When the optical ultrasound probe is in research or clinical uses, the computer will employ the probe and its signal processing unit to determine the phase shift ($\ddot{o}_b$) of ultrasound transmission through the blood flowing in the tubing and the thermistor will report the temperature of blood. Then the computer will pick the factory data file for the hemodialysis machine in use, temperature, and phase measurement to determine from Equation 11 the approximate value of blood density or from Equation 9 and 10 the blood density.

Figure 4:
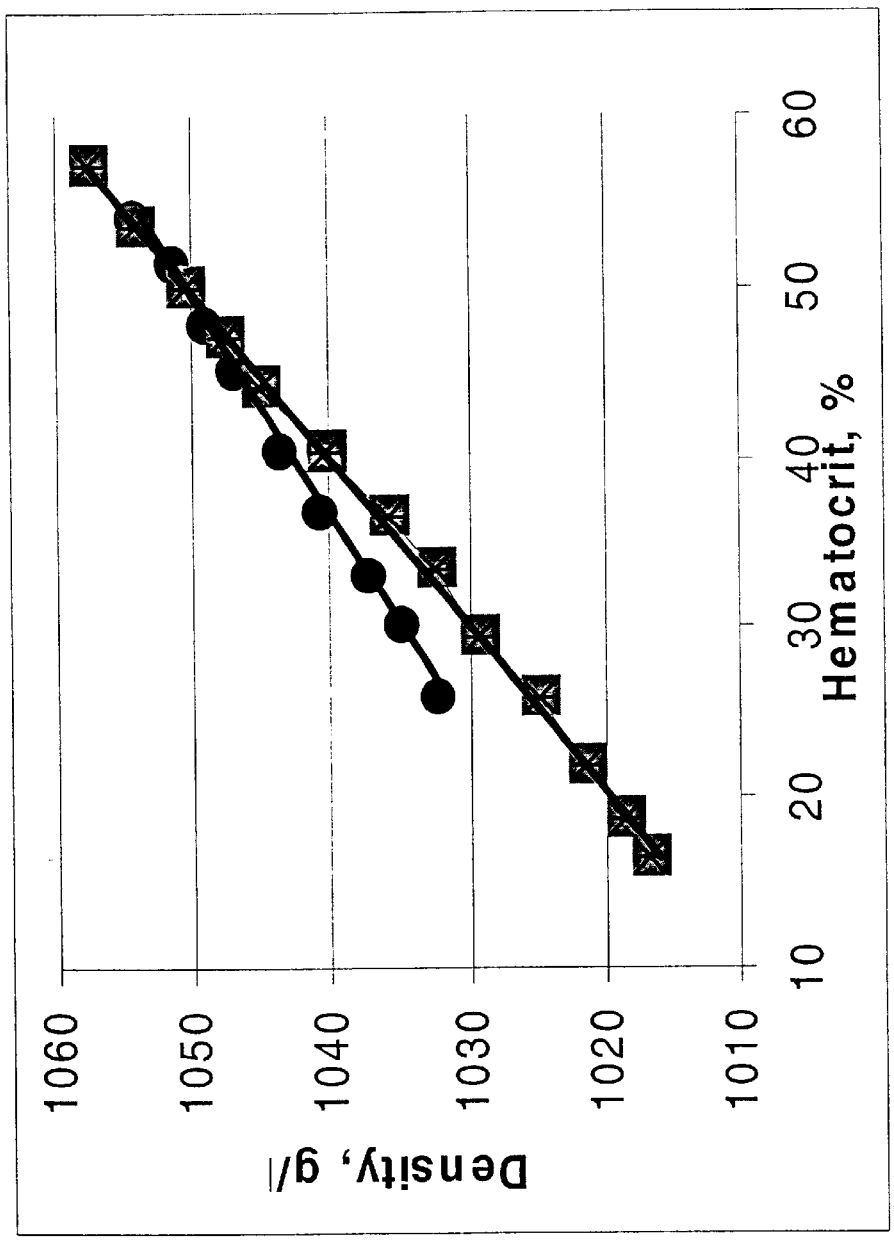
FIG. 4 is a density hematocrit plot when blood in a corporeal circuit is diluted by plasma or saline. The density and hematocrit are measured by the optical ultrasound probe.

When the blood is mixed with a fluid of density $\rho_f$ and no red blood cells, the dilution of the density and hematocrit of blood follows Equation 16.

$$(\tilde{n}_b - \rho_f) = [(\rho_{b,1} - \tilde{n}_f)/H_1]H \quad \text{Equation 16}$$

where $\rho_{b,1}$ is the blood density and $H_1$ is the hematocrit before dilution. The in vitro results performed on a corporeal circuit for saline and plasma dilution are illustrated in FIG. 4.

Right after the connection of the optical ultrasound probe to the hemodialysis circuit and the initiation of the dialysis, the first half hour will be used for the temperature of blood circulating through the circuit and the probe to reach equilibrium. Then a 5 ml of isotonic saline is injected into the arterial port of the circuit and the changes in density are measured through the ultrasound probe, its signal processing unit and the computer. The optical probe measures the absorbance of light as it transmitted through the blood or the reflectance of light as the light is reflected from the blood. These measurements are expressed as optical density (OD). By plotting the change in optical density $\Delta$OD against that of density $\Delta\rho_b$, we can obtain the slope $b_2$ in the linear relationship of Equation 17:

$$\Delta\rho_b = b_2 \Delta OD \quad \text{Equation 17}$$

Its combination with Equation 16 for saline dilution yields Equation 18:

$$\Delta H/H_1 = [b_2/(\rho_{b,1} - \rho_s)]\Delta OD \quad \text{Equation 18}$$

Figure 5A:
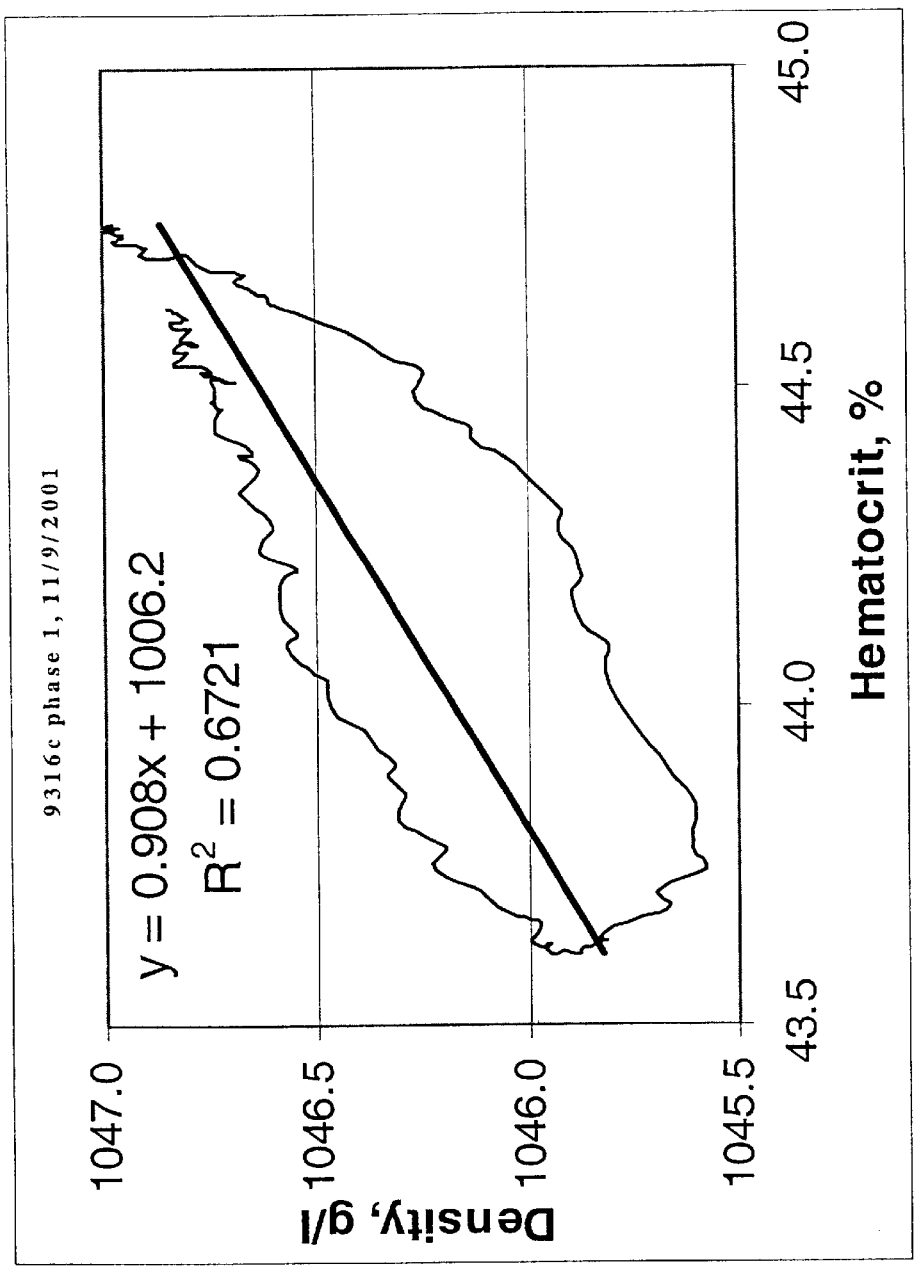
FIG. 5a is a density hematocrit plot following the injection of a saline bolus into the extracorporeal circuit of a hemodialysis machine. The injection was made at the arterial port of the hemodialysis circuit and the density and hematocrit were measured with the probe placement at the venous site of the hemodialysis circuit, which was downstream of the dialyzer.
Figure 5B:
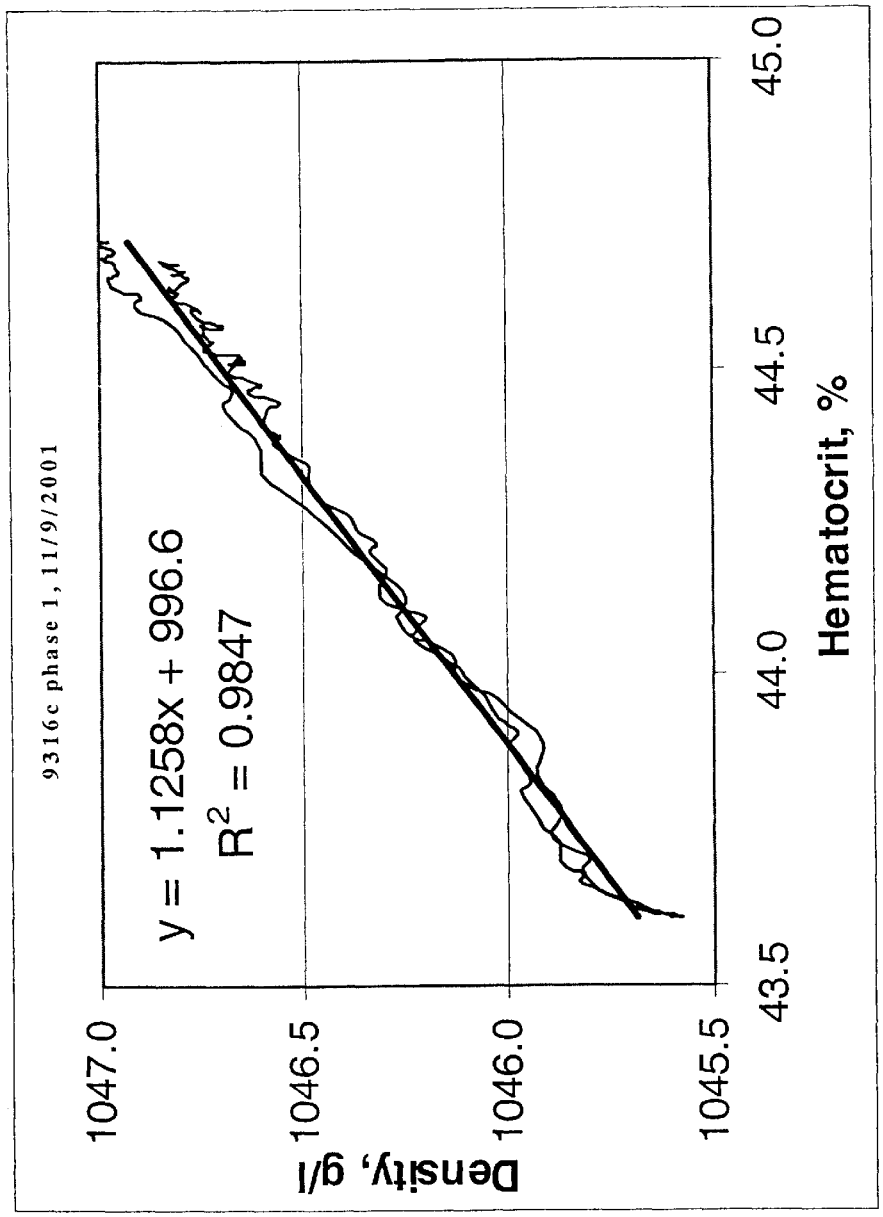
FIG. 5b is the same data of FIG. 5a but with advancement in time for hematocrit.

In practice, the optical probe is located downstream of the ultrasound probe. To carry out the data analysis we will advance the optical signal by a time for which the linear fit between the optical density and density has the correlation coefficient closest to unity. Then the slope of this linear fit is taken as $b_2$. An example of the density plot before the time adjustment is depicted in FIG. 5a and that after the time adjustment is depicted in FIG. 5b. For later measurements, Equation 18 and the slope are used to determine the change in the hematocrit ratio ($\Delta H/H_1$) from the change in measured optical density.

Density dilution methods are well known methods for blood volume determination. A volume of isotonic saline at approximately two to three per cent of the total blood volume is infused into the circulation. The saline density is lower than the blood density and mixing of the saline with the circulating blood leads to a reduction in blood density. Where $\rho_1$ and $\rho_2$ are the density of the blood prior to and after the infusion of isotonic saline, $\rho_s$ is the density of saline and $\Delta V$ is the increase in total blood volume due to the saline infusion. A relationship exists between these densities and the total blood volume ($V_b$) of the patient. This relationship is shown in Equation 19.

$$V_b = A[\Delta V(\rho_2 - \rho_s)/(\rho_1 - \rho_2)] \quad \text{Equation 19}$$

The constant A varies slightly by species and accounts for the Fahraeus effect in the microcirculation. The constant A is approximately equal to 1.14 for human and rabbit and can be determined for any animal. The dilution can be repeated over time, for example every hour, to assess the temporal change in blood volume.

Once the density and hematocrit of the patient are recorded over time, the data will be fitted by polynomial functions of the time to obtain the time course of the density ($\tilde{n}_b$) and that of the hematocrit (H). Then the plasma density fib $\tilde{n}_b$ is calculated by:

$$\tilde{n}_{pl}=(\tilde{n}_b-\tilde{n}_{rbc}H)/(1-H) \qquad \text{Equation 20}$$

where $\tilde{n}_{rbc}$ is the density of red blood cells. Finally the plasma protein concentration ($C_{pl}$) is calculated as:

$$C_{pl}=(\tilde{n}_{pl}-\tilde{n}_s)/0.264 \qquad \text{Equation 21}$$

The unit of this plasma protein concentration is in grams of protein per liter of plasma. Expressing through the change in hematocrit and that in density, the change in plasma density is given by Equation 22.

$$\Delta\tilde{n}_{pl}=\Delta\tilde{n}_b/(1-H)-(\tilde{n}_{rbc}-\tilde{n}_b)\Delta H/(1-H)^2 \qquad \text{Equation 22}$$

Equation 16. specifies that the dilution of blood by a fluid with a density $\rho_f$ will have in a hematocrit density plot a slope of $(\rho_{b,1}-\rho_f)/H_1$. The particular result of FIG. 5b provides a slope characterizing the process of saline dilution. If the subsequent measurements yield a density hematocrit plot with a slope smaller than that in FIG. 5b, we may conclude that the blood is diluted with a fluid density larger than that saline. (The fluid density relates to saline density and protein concentration of the fluid through Equation 21.)

There are two clinical protocols that the physician can use to assess blood volume, change in blood volume, and microvascular pooling. First clinical protocol prescribes the performance of one blood volume measurement at the beginning of the hemodialysis session and another at the end of the session. These two measurements determine the change in blood volume ($\rho V_b$). In the time between these two measurements, the compressibility probe monitors the blood density and the dialysis machine will report the ultrafiltrate removed from the patient as $\Delta V_{dialysis}$. If the blood density right after the first blood volume measurement is defined as $\rho_4$ and the blood density before the second blood volume measurement is defined as $\rho_5$, the corresponding hematocrits are $H_4$ and $H_5$. Then the pooling of the blood to the microcirculation can be calculated from Equation 23.

$$\Delta V_{pooling}=B\{V_b(\rho_4-\rho_5)F_{cell}/(\rho_4-\rho_{pl})+(\Delta V_{dialysis}-2\Delta V_b)[(1-H_4)/(1-F_{cell}H_4)](\rho_{pl}-\rho_s)/[3(\rho_4-\rho_{pl})]-\Delta V_b\} \qquad \text{Equation 23}$$

where $\rho_{p1}$ is the density of plasma right after the first blood volume measurement and $\rho_s$ is the density of the ultrafiltrate or saline, the constant $F_{cell}$ is 0.87, the constant B is 2.78. The amount of pooling is indicative of how the patient is susceptible to microvascular pooling.

The second clinical protocol uses the time course of the measured density and hematocrit to determine the slope of the hematocrit density plot, the change in total blood volume ($\ddot{A}V_b$) and the volume pooled to the microcirculation ($\ddot{A}V_{pooling}$). In reference to the initial density and hematocrit right after temperature equilibrium, the change in blood density, hematocrit and plasma density from their initial value is identified as $\ddot{A}\tilde{n}_b$, $\ddot{A}H$, and $\ddot{A}\tilde{n}_{p1}$ respectively. $\ddot{A}V_b$ and $\ddot{A}V_{pooling}$ are to be calculated by Equation 24 and 25:

$$\ddot{A}V_b/V_b=(3/2)[\ddot{A}\tilde{n}_{pl}/(\tilde{n}_{pl}-\tilde{n}_s)](1-F_{cell}H)-\frac{1}{2}(\ddot{A}V_{dialysis}/V_b) \qquad \text{Equation 24}$$

$$\ddot{A}V_{pooling}/V_b=3.46\{F_{cell}\ddot{A}H/H-[(1-H)/H]\ddot{A}V_b/V_b\} \qquad \text{Equation 25}$$

The change in the blood volume of macrocirculation is now determined by Equation 26:

$$\ddot{A}V_{macro}/V_b=\ddot{A}V_b-\ddot{A}V_{pooling} \qquad \text{Equation 26}$$

This change serves as an index on how well cardiac filling is accomplished while the slope of the hematocrit density plot serves as an index on the exchange of fluid and protein between the tissue and blood compartment.

There are several working models of the ultrasound system to assess blood density. In one signal processing embodiment the transducer 16 is activated by any commercially available pulser/receiver, including a Panametrics 5072PR pulser/receiver, to emit ultrasound impulses of about 15 to 20 Megahertz at a rate of about 100 Hertz. After its transmission through the flowing blood, the second transducer 18 receives the ultrasound signal. The trigger signal from the pulser/receiver triggers a digital oscilloscope such as a LeCroy 9350AL oscilloscope or a Synatec A/D converter to sample the signal from the receiver 18 at 100 Megahertz to 1 GigaHertz. Cabling and connectors 20 are shown to connect the transducers 16 and 18 to the electronic devices. The digitized samples so triggered are transferred to a computer for the determination of the phase shift and the calculation of sound velocity using the equations described herein. In another embodiment, the signals from the receiving transducer and the function generator to excite the emitting transducer are processed by a Phase Lock Amplifier such as Stanford Research System SR 844, to obtain the phase shift. Through a calibration of the shift as a function of density, the system can then be used to assess blood density.

In a preferred embodiment, the optical ultrasound probe system is constructed with a novel ultrasound signal processing unit, a simple computation scheme, and a two-media calibration procedure that are specifically designed to process the ultrasound signals for phase shift and subsequently density determination. In one design, a dual channel A/D converter is used to sample the data at 65 MSPS and an ultrasound at the frequency of 5.417 Megahertz. The digitized data are multiplied and summed in accordance with Equations 3, 4 and 5 for the determination of the phase shift. For this case, the value of j used in Equation 4 is 3. (If a frequency of 3.25 or 4.063 Megahertz is used, the value of j will be 5 or 4 respectively.) When A/D converters having a sampling rate of 105 MSPS are used in another design, an ultrasound frequency of 5.25 Megahertz and a value of 5 for the j in Equation 4 will be used. (Similarly the use of a frequency 3.281, 3.75, or 4.375 Megahertz will have a value of 8, 7 or 6 for j respectively.) After the signal processing to determine the phase shift, the use of Equation 11 and the data file from the factory allows the computer to determine the blood density. Working together with the optical probe, the measurement of density and hematocrit can now be used to determine plasma protein concentration. One can also determine from the change in density and hematocrit the blood volume, change in blood volume, and blood volume pooled to the microcirculation.

Conventionally, the 90-degree shift of the excitation signal in Equation 4 is accomplished by electronic means. The above digitized scheme and the frequency selected for sampling and excitation allow us to accomplish the 90-degree shift of the excitation signal by simply changing the index used in the summation processing of Equation 4. This data manipulation simplifies the electronics of the ultrasound signal-processing unit considerably. The processing unit and the computer process ultrasound signals of 3 to 5 Megahertz to achieve a resolution in time shift of the order of 0.05 nanosecond.

An excitation signal is generated by the signal generator in the ultrasound signal-processing unit 54 as shown in FIG. 3 that is identical to the ultrasound wave 30 emitted by the transducer of FIG. 2. A second signal is transmitted by the receiving transducer 24 as it receives the ultrasound wave, which has been transmitted through the wall of the tube 14 and blood. The ultrasound signal-processing unit 54 and the computer 58 process the excitation and receiving signal for the determination of the phase shift of the two signals. The division of the phase shift by f·360° is the time shift $T_{shift}$ between the excitation and received signals shown in FIG. 2. For the purpose of illustration, the ultrasound peak 34 is transmitted to become the peak 36. The overall time delay (i.e. peak to peak time shift) on ultrasound transmission is the sum of the time shift ($T_{shift}$) and a multiple of ultrasound period ($nT_0$). After this adjustment of phase shift, it is processed through Equation 9 to determine the sound velocity, then Equation 10 the density and finally Equation 2 the compressibility. One can also obtain an approximate density through Equation 11.

The integration of the clip-on ultrasound optical probe with a dialysis system is shown schematically in FIG. 3. Tubing 14 leads from a blood vessel of a patient to an extracorporeal system 48 such as a dialysis system with a pump, a bubble trap and a hemodialysis filter. In the illustrated embodiment, the blood vessel is an artery 40 of a patient. A portion of the blood 46 flowing through the artery 40 is drawn into the tubing 14 for delivery through the clip-on ultrasound optical probe 26 to the extracorporeal system 48. Between the probe 26 and the extracorporeal system 48, the tubing 14 is connected to a saline bag 44, which contains a fixed amount of saline. Normally, a hemostat 50 clamps up the tubing connecting the saline bag to the tubing 14. For the infusion of saline into the circulation, the release of hemostat 50 will allow the pump in the extracorporeal system 48 to withdraw the saline in bag 44 into the circulation. The bag 44 is prepackaged with 50, 100, 150 or 200 ml of saline, which is selected according to the body weight of the patient. The connection to bag 44 will be re-clamped by the hemostat after the completion of infusion within about one-half minute. The saline-enriched blood 12 is returned to the patient's circulation through the connection to a blood vessel, such as the illustrated vein 42. The transducers 22 and 24 in the clip-on probe 26 respectively emit and receive the ultrasound waves which are passed via cabling 20 to the ultrasound signal-processing unit 54. The digitized information is relayed via cabling 56 to the computer 58 where overall transmission time, sound velocity, compressibility and density are continuously computed. The diode 62 in the clip-on probe 26 emits light and diodes 64 and 66 receive absorbed or reflected light. Delivered via the optical signal-processing unit 70 through cable 74, the optical density is used by computer 58 for the determination of hematocrit. The temperature signal from the thermistor 28 is directly transmitted to the computer 58. The temperature is used to correct the density assessment to the same temperature for the computation of the density change produced by a saline dilution procedure or by the patient's response to treatment. Temperature is incorporated in the calculations using the equations described herein.

Additional embodiments of the clip-on ultrasound optical probe will become apparent to those of ordinary skill in the art.

What is claimed is:

1. A process for monitoring changes in blood volume and microvascular pooling in animals, comprising:
   an extracorporeal blood treatment device in which blood from a blood system is conducted through a first branch of said extracorporeal system which is connected by tubing to an arterial segment of said blood system into a dialyzer or filter and returned via a second branch of said extracorporeal system with the said second branch connected by tubing to a venous segment of said blood system;
   a diagnostic apparatus attached to said tubing wherein said diagnostic apparatus emits and receives an ultrasound wave and a light wave through blood flowing through said extracorporeal system;
   a signal processing system, wherein said signal processing system initiates and records ultrasound waves and light transmissions, determines phase shift between emitting and receiving ultrasound waves, monitors with high resolution sound velocity, density, compressibility, and optical density of blood, hematocrit, and plasma protein concentration, and assesses changes in said sound velocity, density, compressibility, optical density, hematocrit, and plasma protein concentration of modified blood at an equivalent temperature
   an infusion system, wherein a known amount of an indicator fluid is infused into said blood system at an injection connection located downstream of said diagnostic apparatus, and wherein infusion of said indicator fluid into said blood system changes the density of said blood system as measured through said diagnostic apparatus and said signal processing system;
   a calibration procedure; and
   a computing system for determining blood volume, changes in blood volume, changes in plasma protein concentration, and microvascular pooling from said hematocrit and density change.

2. The process of claim 1 wherein said signal processing system includes an ultrasound signal processing unit, an optical signal processing unit, an ultrasound and light generator, and two dual channel A/D converters.

3. The process of claim 2, wherein said calibration procedure employs two fluids of known sound velocity to determine the relationship between the phase shift generated by the transmission of the ultrasound through the blood and the sound velocity of blood for the assessment of compressibility and density of blood.

4. The process of claim 2, wherein said calibration procedure employs a saline injection process to match the optical density measured by said optical processing unit with the density measurements made by said ultrasound signal processing unit as a procedure to calibrate optical density in terms of hematocrit.

5. The process of claim 1 wherein said animal is a human.

6. The process of claim 1 wherein said diagnostic apparatus is a clip-on probe having mounted thereon at least one ultrasound emitting transducer, at least one ultrasound receiving transducer, at least one light emitting diode, and at least two photodiodes.

7. The process of claim 6 wherein said diagnostic apparatus further comprises a thermistor, wherein said thermistor takes a temperature measurement that is incorporated into a computation to convert measured sound velocity to density of blood.

8. The process of claim 6 wherein said diagnostic apparatus is clipped onto the tubing of said extracorporeal blood treatment system.

9. The process of claim 1 wherein said indicator fluid is isotonic saline or dialysate.

10. The process of claim 9 further comprising a dilution procedure wherein a known volume of said saline or dialysate is infused into said blood system for use in computing blood volume of the animal.

11. The process of claim 6 wherein said at least one ultrasound emitting transducer, said at least one ultrasound receiving transducer, said at least one light emitting diode, and said at least two photodiodes are tightly clipped onto said tubing of said extracorporeal system for transmission of ultrasound and light.

12. The process of claim 2 wherein said ultrasound wave of specific frequency is processed by said ultrasound signal-processing unit and said computer memory unit using a novel computation scheme to determine the phase shift between emitting and receiving ultrasound.

13. A method for monitoring a patient's cardiovascular function through use of an optical ultrasound probe.

14. The method of claim 13 wherein said monitoring comprises calculating blood volume from density changes in blood flowing through an extracorporeal system as detected by said optical ultrasound probe.

15. The method of claim 14 wherein repeated dilutions are introduced into said blood to assess blood volume changes on hourly basis over the course of treatment.

16. The method of claim 13 wherein said monitoring comprises calculating microvascular pooling from changes in density and hematocrit produced by redistribution of blood and plasma volume in a patient's circulation as detected by an optical ultrasound probe.

17. A process for monitoring changes in blood volume and microvascular pooling in animals, comprising:

a diagnostic apparatus attached to a blood system wherein said diagnostic apparatus emits and receives an ultrasound wave and a light wave through blood flowing through an extracorporeal system;

a signal processing system, wherein said signal processing system determines a phase shift between said emitting and receiving ultrasound wave, and determines absorbance and reflectance of said light wave;

at least two control units within said signal processing system for detecting compressibility, density, hematocrit and plasma protein concentration with high resolution, for assessing changes in said compressibility, density, hematocrit, and plasma protein concentration at an equivalent temperature, for initiating and recording ultrasound and light waves, and for monitoring physical parameters of modified blood; and a computer memory unit for determining blood volume and microvascular pooling from said hematocrit and density change.

18. The process of claim 17 wherein said animal is a human.

19. The process of claim 17 wherein said diagnostic apparatus is a clip-on probe having mounted thereon at least one ultrasound emitting transducer, at least one ultrasound receiving transducer, at least one light emitting diode, and at least two photodiodes.

20. The process of claim 19 further comprising a thermistor attached to said diagnostic apparatus.

21. The process of claim 19 wherein said diagnostic apparatus is clipped onto said a tubing of said extracorporeal system connecting an artery and a vein of said animal.

* * * * *